US00PP35581P2

(12) United States Plant Patent
Schara

(10) Patent No.: US PP35,581 P2
(45) Date of Patent: Jan. 16, 2024

(54) ***SEMPERVIVUM* PLANT NAMED 'VS2023-01'**

(50) Latin Name: *Sempervivum hybrida*
Varietal Denomination: VS2023-01

(71) Applicant: Volkmar Schara, Herrieden (DE)

(72) Inventor: Volkmar Schara, Herrieden (DE)

( * ) Notice: Subject to any disclaimer, the term of this patent is extended or adjusted under 35 U.S.C. 154(b) by 0 days.

(21) Appl. No.: 18/114,715

(22) Filed: Feb. 27, 2023

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./263.1, 373
See application file for complete search history.

(56) References Cited

PUBLICATIONS https://mountaincrestgardens.com/sempervivum-heuffelli-jade/ Retrieved from the Internet on Jun. 13, 2023.*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new and distinct variety of *Sempervivum* named 'VS2023-01' that is characterized by fast-growing single rosette of thick succulent leaves arranged in whorls. In the current year of growth, the leaves of 'VS2023-01' are dark purple in color with mid green tips. The two year old leaves of 'VS2023-01' form the lowermost whorls and have developed orange-grey tips. The new foliage growth which emerges in the center of the rosette is green in color. Two year old plants of 'VS2023-01' develop offsets which may be removed for propagation. 'VS2023-01' is hardy to USDA Zone 4.

1 Drawing Sheet

Genus and species: *Sempervivum hybrida.*
Variety denomination: 'VS2023-01'.

BACKGROUND OF THE NEW PLANT

The present invention relates to a new variety of *Sempervivum* commonly known as Stonecrop, or Hens and Chicks, or Houseleek. The present invention is known botanically as *Sempervivum hybrida* and will be referred to hereinafter by the cultivar name 'VS2023-01'.

*Sempervivums* are hardy perennial succulent plants which are grown and appreciated for the diversity of color and form in their foliage and for their tolerance of arid conditions. Many cultivars of *Sempervivum* are in commerce and involve a wide range of species and natural hybrids. *Sempervivums* are versatile in use and are grown in dry soils, rock gardens, and in containers. The genus *Sempervivum* is a member of the family Crassulaceae.

The inventor maintains in his nursery in Herrieden, Ansbach, Germany a large collection of *Sempervivums* including named varieties and unnamed and unreleased seedlings raised by the inventor. The inventor established his *Sempervivum* breeding programme in 1996 with the primary aim of developing a series of colorful varieties which form uniform large fast-growing rosettes with minimal production of offsets and flowers.

The inventor selected 'VS2023-01' in 1998 as a seedling which the inventor had raised from seed resulting from the open pollination of the inventor's variety *Sempervivum* 'Leopold' (unpatented), as female female parent. The identity of the male parent is unknown. 'VS2023-01' was first asexually propagated in 2014 by the inventor at the inventor's nursery by removal of lateral offsets (known also as chicks or pups) and rooting the offsets in well-drained soil. Since that time, under careful observation, the distinguishing characteristics of 'VS2023-01' have been determined stable and uniform and reproduced true to type in successive generations of asexual propagation.

SUMMARY

The following traits have been repeatedly observed and represent the distinguishing characteristics of the new *Sempervivum* variety named 'VS2023-01'. These traits in combination distinguish 'VS2023-01' from all other existing varieties of *Sempervivum* known to the inventor. 'VS2023-01' has not been tested under all possible conditions. Phenotypic differences may be observed with variations in environmental, climatic, and cultural conditions.

1. Plants of 'VS2023-01' exhibit a fast-growing single rosette of thick succulent leaves arranged in whorls.
2. In the current year of growth, the leaves of 'VS2023-01' are dark purple in color with mid green tips.
3. The two year old leaves of 'VS2023-01' form the lowermost whorls and have developed orange-grey tips.
4. The new foliage growth which emerges in the center of the rosette is green in color.
5. Two year old plants of 'VS2023-01' develop offsets which surround and are attached to the base of the original rosette. These offsets may be removed for propagation.

6. Flowers of 'VS2023-01' have not been observed.
7. 'VS2023-01' is hardy to USDA Zone 4.

COMPARISON WITH PARENTAL LINES AND KNOWN VARIETY

The inventor selected 'VS2023-01' for its rapid production of very large rosettes compared to the many varieties in commerce. The inventor considers that two varieties of *Sempervivum* exhibit this characteristic: the female parent *Sempervivum* 'Leopold' and also the variety *Sempervivum* 'Ruben'. Whereas both 'Leopold' and 'Ruben' produce a rosette of foliage which is uniformly red-purple in color when juvenile and mature, the new foliage growth of 'VS2023-01' is green in color and the mature foliage of 'VS2023-01' is dark purple in color with mid green tips.

BRIEF DESCRIPTION OF THE PHOTOGRAPH

The accompanying photograph, illustrates a two-year-old plant of 'VS2023-01' which is growing in a 2-gallon container out of doors in Santa Barbara, California. The photograph was taken in late August 2022.

BOTANICAL DESCRIPTION OF THE PLANT

The following is a detailed botanical description of the new *Sempervivum* variety named 'VS2023-01'. Observations, measurements, values and comparisons were collected in Santa Barbara, California in August 2022 from a two-year-old plant which has been grown out of doors in a 2-gallon container. Color determinations are made in accordance with the 2007 edition of The Royal Horticultural Society Colour Chart from London, England, except where general color terms of ordinary dictionary significance are used. The growing requirements of the new variety 'VS2023-01' are similar to the species.

The observed plant consists of a large central rosette surrounded small offsets attached to the base of the central rosette. The offsets have not been removed. Except where the offsets are described herein, the botanical description is drawn from the central rosette.

Botanical classification:
- *Family.*—Crassulaceae.
- *Genus and species.*—*Sempervivum hybrida.*
- *Denomination.*—'VS2023-01'.
- *Common names.*—Stonecrop, Hens and Chicks, Houseleek.

Parentage:
- *Female parent.*—*Sempervivum* 'Leopold'.
- *Male parent.*—Unknown.

Plant:
- *Habit.*—Basal rosette.
- *Use.*—Garden and landscape planting, especially in dry conditions, planted containers.
- *Suggested commercial container size.*—4-inch container (1-year-old plants), 2-gallon container (2-year-old plants).
- *Propagation method.*—Removal and rooting of offsets.
- *Rooting system.*—Fine and fibrous.
- *Root color.*—NN155C.
- *Vigor.*—Fast-growing through spring and early summer.
- *Crop time.*—A 4-inch container will be filled out after four (4) months from planting a rooted offset. A two-gallon container will be filled out after two years from planting a rooted offset.
- *Plant dimensions* (*two-year-old plant, 2-gallon container*).—11 cm in height and 17 cm in diameter (excluding offsets) and 23 cm in diameter including the offsets.
- *Cultural requirements.*—Grown in free-draining soil and water sparingly in morning or evening.
- *Pest and disease resistance.*—None known to the inventor.
- *Pest and disease susceptibility.*—None known to the inventor.
- *Hardiness.*—USDA Zone 4.

Stem: Stemless.

Foliage:
- *Arrangement.*—Leaves arranged in whorls.
- *Whorl quantity.*—15 whorls distinguishable, further whorls are developing in the deep center of the plant.
- *Leaf quantity per whorl.*—11-15.
- *Leaf attachment.*—Sessile.
- *Leaf texture.*—Succulent, fleshy.
- *Leaf division.*—Simple.
- *Leaf margin.*—Finely ciliate, hairs evenly spaced 0.25 mm-0.5 mm apart, length 0.25 mm — 0.5 mm, angled towards base, color NN155D.
- *Leaf surface:* (*abaxial and adaxial*).—Glabrous, semi-glossy.
- *Leaf shape.*—Obovate.
- *Leaf length* (*largest leaves*).—50 mm.
- *Leaf width* (*largest leaves*).—22 mm.
- *Leaf thickness* (*largest leaves*).—6 mm towards base, 2.5 mm towards apex.
- *Leaf color.*—
- *Oldest leaves* (*formed in previous season and comprising the lowermost and largest whorls, both surfaces*).—59A towards base, 146C in mid-section, ranging between 173C and 170C towards apex.
- *Current year leaves* (*forming the central and inner whorls, both surfaces*).—187A except tips towards apex. Tip color 146D.
- *Young leaves within tight rosette, unexposed to sunlight, both surfaces.*—146D.
- *Leaf apex.*—Mucronate, spine 2 mm-3 mm in length, soft, spine color 173A except youngest leaves, spine color 146D.
- *Leaf base.*—Truncate.
- *Venation.*—Absent.

Offsets:
- *Offset description.*—Offsets emerge in second and subsequent years as whole plant rosettes attached to the base of the primary rosette. Initially, offsets are stemless then developing stems with age. Occasional offsets are borne on stems which originate below the soil surface. Offsets may be removed with stems attached for propagation.
- *Offset quantity.*—14 on observed plant.
- *Offset stem dimensions* (*if not removed*).—Up to 10 cm in length, 4 mm in diameter.
- *Offset dimensions.*—Ranging between 2 cm and 7 cm in diameter and between 1 cm and 3 cm in height.
- *Offset foliage description.*—Whorled, older leaves colored 187A except tips 146D, youngest leaves 146D.

Inflorescence: No inflorescences have been observed on the two year old plants.
- *Inflorescence type.*—Terminal cyme.

*Inflorescence dimensions.*—6 cm in height, 5 cm in diameter.
*Blooming season.*—Late summer or fall.
*Inflorescence quantity* (*if present*).—1 or 2.
*Inflorescence stems* (*peduncles*).—Initially upright, emerging from within the rosette of whorls, not from the base. Stems arch as inflorescence ages and dies.
*Stem texture.*—Fleshy, surface downy.
*Stem dimensions.*—20 cm-30 cm in length, 3 mm-5 mm in diameter.
*Stem color.*—144D-145A.
*Flower quantity.*—Approximately 50 per cyme.
*Flower shape.*—Stellar, radially symmetrical.
*Flower dimensions.*—5 mm in height, 6 mm in diameter.
*Fragrance.*—None observed.
*Lastingness of individual flower* (*on the plant*).—10-14 days.
*Persistent or self-cleaning.*—Persistent.

Bud:
*Bud shape.*—Spherical.
*Bud dimensions* (*immediately prior to opening*).—3 mm-4 mm in diameter.
*Bud surface.*—Pubescent.
*Bud apex.*—Rounded.
*Bud color.*—26B.

Petals:
*Petal quantity.*—16.
*Petal color* (*both surfaces*).—36D, becoming NN155C when flower is fully expanded.
*Petal shape.*—Lanceolate.
*Petal apex.*—Acute.
*Petal base.*—Truncate.
*Petal margin.*—Smooth, entire.
*Petal dimensions.*—5 mm in length, 1 mm in width.
*Petal surface texture.*—Matte, paper-like.

Sepals:
*Sepal quantity.*—16.
*Sepal shape.*—Lanceolate.
*Sepal color.*—Ranges between 34A and 34C except 46A towards apex.
*Sepal apex.*—Acute.
*Sepal base.*—Truncate.
*Sepal margin.*—Smooth, entire.
*Sepal dimensions.*—3 mm-4 mm in length, 1 mm in width.
*Sepal surface texture.*—Matte, abaxial surface pubescent.

Pedicel:
*Pedicel shape.*—Cylindrical.
*Pedicel color.*—34C.
*Pedicel surface texture.*—Glabrous.
*Pedicel dimensions.*—8 mm in length and 2 mm in width.

Reproductive organs:
*Stamens.*—24-32 in number, arranged in one or two concentric rings around central pistil cluster.
*Filaments.*—3 mm-4 mm in length, color 46B.
*Anthers.*—Develop within orange-red membrane, color 45C.
*Pollen.*—Appears as membrane is shed, color 9A and bright, quantity moderate.
*Pistils.*—Approximately 12 in number.
*Style.*—Approximately 3 mm in length, color 17C.
*Stigma.*—Conical, color 34C.
*Ovary.*—Not observed.

Seed: Extremely fine, dust-like, color dark grey.

I claim:

1. A new and distinct cultivar of *Sempervivum* Plant Named 'VS2023-01' as described and illustrated herein.

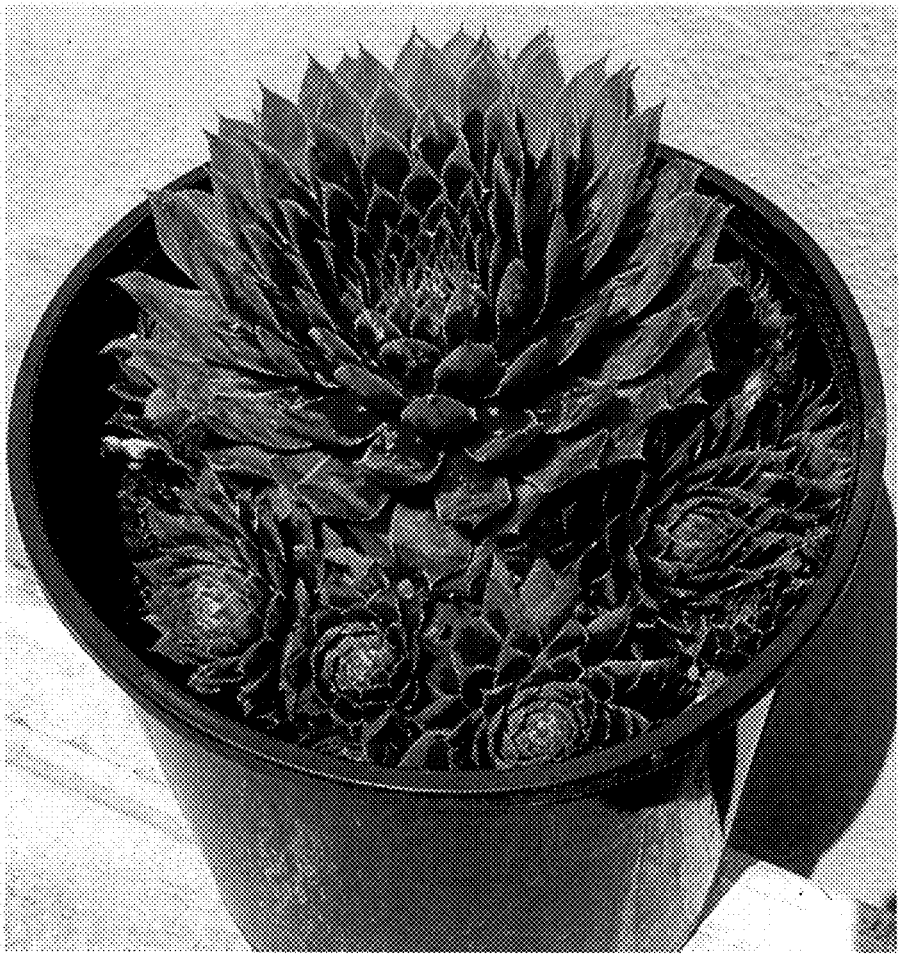

* * * * *